US010113240B2

(12) United States Patent
Miller et al.

(10) Patent No.: US 10,113,240 B2
(45) Date of Patent: Oct. 30, 2018

(54) CATHODIC PROTECTION SYSTEM MONITORING

(71) Applicant: Stratocom Solutions Corporation, Kelowna OT (CA)

(72) Inventors: Darren Lee Miller, Kelowna (CA); Michael William Novakowicz, Peterborough (CA); Haydn Russell Wintersgill, Leduc (CA)

(73) Assignee: Stratocom Solutions Corporation (CA)

( * ) Notice: Subject to any disclaimer, the term of this patent is extended or adjusted under 35 U.S.C. 154(b) by 0 days.

(21) Appl. No.: 15/435,226

(22) Filed: Feb. 16, 2017

(65) Prior Publication Data

US 2018/0230605 A1    Aug. 16, 2018

(51) Int. Cl.
   *C23F 13/02* (2006.01)
   *C23F 13/22* (2006.01)
   (Continued)

(52) U.S. Cl.
   CPC .............. *C23F 13/22* (2013.01); *C23F 13/10* (2013.01); *F17D 5/00* (2013.01); *C23F 2213/32* (2013.01); *H04W 4/70* (2018.02)

(58) Field of Classification Search
   CPC .......... C23F 13/02; C23F 13/04; C23F 13/08; C23F 13/10; C23F 13/22; C23F 2213/10; C23F 2213/32; F17D 5/00
   See application file for complete search history.

(56) References Cited

U.S. PATENT DOCUMENTS

| 6,933,857 B2 | 8/2005 | Foote |
| 6,992,594 B2 | 1/2006 | Dudley |
| 7,068,052 B2 | 6/2006 | Hilleary et al. |
| 7,633,302 B2 | 12/2009 | Peters |

(Continued)

FOREIGN PATENT DOCUMENTS

| CA | 2258360 A1 | 8/1999 |
| CN | 105140823 | 12/2015 |

(Continued)

OTHER PUBLICATIONS

Techopedia (Rectifier).*

(Continued)

*Primary Examiner* — Alexander W Keeling
(74) *Attorney, Agent, or Firm* — Prasad IP, PC

(57) ABSTRACT

A method and system is disclosed for testing a cathodic protection system that protects a metallic structure with one or more DC power sources electrically connected to the metallic structure and an associated reference electrode. The metallic structure may be cathodically protected at multiple locations. A Cathodic Protection Waveform Monitoring Unit (CPWMU) operates independently from power cycling by the cathodic protection system to measure cathodic protection voltage levels by measuring, over one or more measurement time periods, a voltage differential between the metallic structure and its associated reference electrode, a plurality of times when power provided to the metallic structure is cycled on and off. The CPWMU includes digital storage to store values indicative of the measured voltage differentials over the measurement time period. A Cathodic Protection Waveform Reader (CPWR) that may be remotely located from any CPWMU communicates with a number of CPWMU's within communication range to obtain the values stored in the CPWMUs. The CPWR may be positioned in a variety of aircraft, vehicles or be hand carried.

19 Claims, 9 Drawing Sheets

(51) Int. Cl.
*C23F 13/10* (2006.01)
*F17D 5/00* (2006.01)
*H04W 4/70* (2018.01)

(56) References Cited

U.S. PATENT DOCUMENTS

| | | | |
|---|---|---|---|
| 2002/0196160 A1 | 12/2002 | Hilleary | |
| 2007/0035315 A1* | 2/2007 | Hilleary | C23F 13/22 324/700 |
| 2011/0238347 A1* | 9/2011 | Gemperli | C23F 13/04 702/65 |
| 2015/0163849 A1 | 6/2015 | Bauer et al. | |
| 2015/0169462 A1* | 6/2015 | Vaisanen | G06F 21/78 711/166 |

FOREIGN PATENT DOCUMENTS

| | | |
|---|---|---|
| WO | 2015195858 A1 | 12/2015 |
| WO | 2018150273 A1 | 8/2018 |

OTHER PUBLICATIONS

Dick Baxter, Jim Britton, Offshore Cathodic Protection 101: What It Is and How It Works., Deepwater Corrosion Services, Inc., www.stoprust.com, 2006.
R. L. Kean, K. G. Davies, Cathodic Protection, Department of Trade and Industry.
Written Opinion of the International Searching Authority for PCT/IB2018/000251 (Form PCT/ISA/237), dated Sep. 7, 2018.

* cited by examiner

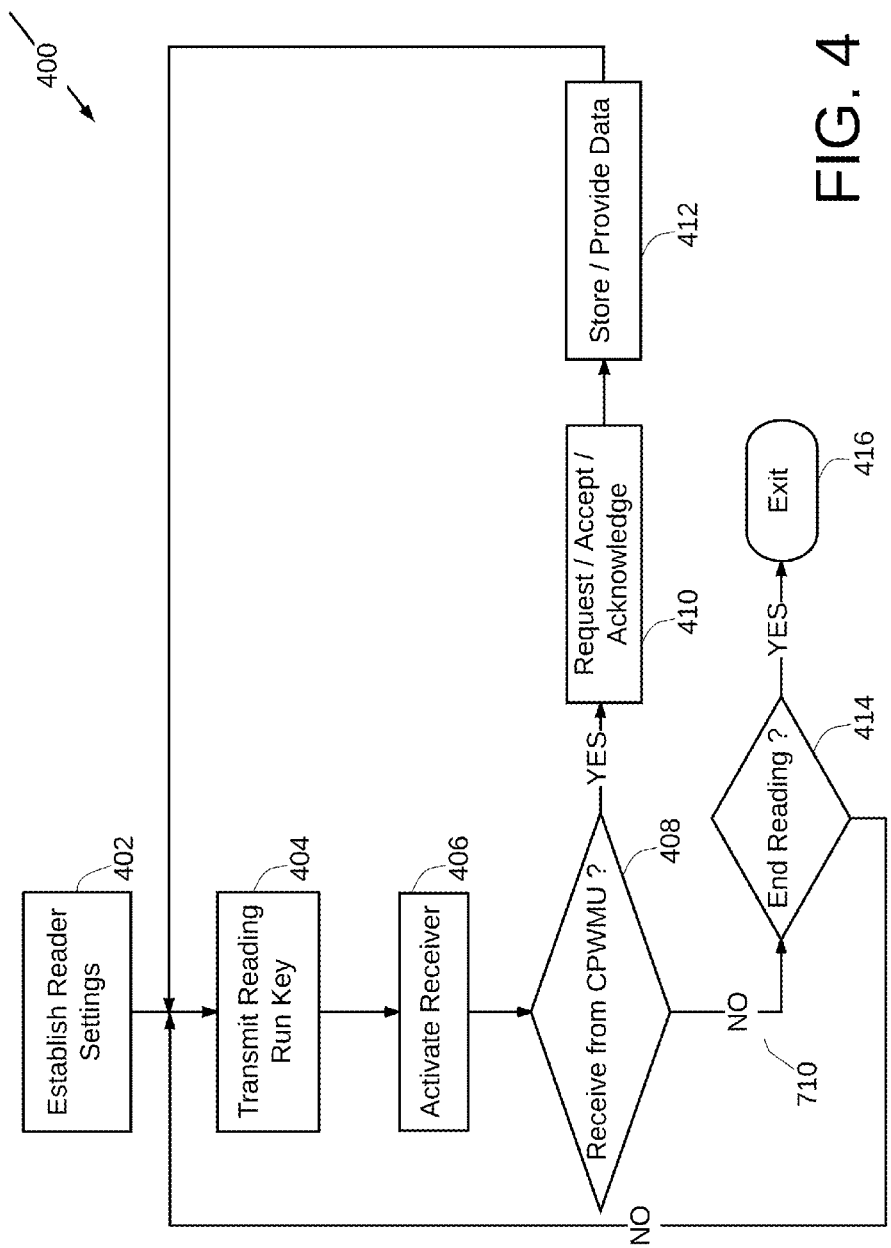

CATHODIC PROTECTION SYSTEM MONITORING

FIELD OF THE DISCLOSURE

This disclosure relates generally to the field of cathodic protection systems and more particularly to monitoring of cathodic protection systems.

BACKGROUND

Pipeline, utility and infrastructure companies have traditionally employed a manpower intensive approach to reading and recording of the effectiveness of their corrosion control systems. Typically, these companies employ large numbers of company personnel or consultants who work selected routes to walk or drive urban and rural areas to acquire information to verify the effectiveness of corrosion control measures that are being undertaken.

The problems faced by these companies are numerous. First, to meet government and industry regulations, readings must be taken at mandated intervals to prove the effectiveness of the corrosion control measures being undertaken. For example, high pressure pipeline companies must take readings on all test point locations throughout the system, typically multiple reads every mile, at monthly or yearly intervals. One example of regulations that may govern underground or submerged pipelines is the standard NACE SP0169 developed by NACE International, 1440 South Creek Drive, Houston, Tex. USA (www.nace.org). Utility companies take multiple reads in a sample of locations, at approximately the same intervals distributed throughout their low-pressure metallic distribution systems. Other infrastructure companies have similar requirements. The cost of the labor force conducting these surveys can be quite high. Secondly, the infrastructure that is required to transport the technicians to these locations is quite expensive and may not be the best use of the resources of the company. The transportation and subsistence costs for these surveys accounts for as much as 40-50% of the total expenses associated with the operation and reporting of the corrosion control systems. Additionally, accidents with the vehicles, replacement costs, insurance and routine maintenance, and the price of fuel further increase overall costs.

BRIEF DESCRIPTION OF THE DRAWINGS

The accompanying drawings, which are incorporated in and constitute a part of this specification exemplify the embodiments of the present invention and, together with the description, serve to explain and illustrate principles of the inventive techniques disclosed herein. Specifically:

FIG. 4 is a flowchart illustrating operation of an embodiment of a Cathodic Protection Waveform Reader (CPWR).

DETAILED DESCRIPTION

Figure 1:
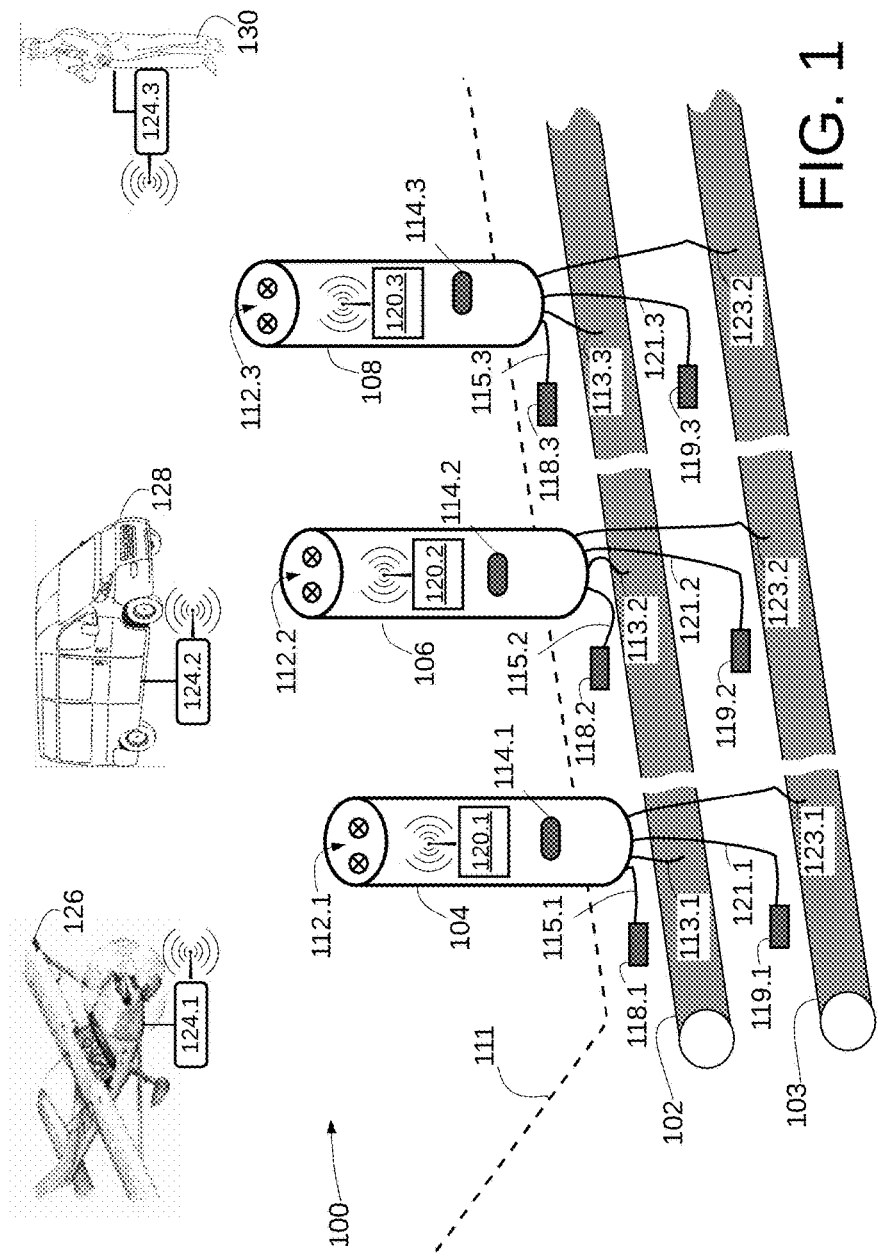
FIG. 1 illustrates two underground pipelines with cathodic protection and monitoring at a plurality of locations.

In the following detailed description, reference will be made to the accompanying drawings, in which identical functional elements are designated with like numerals. The aforementioned accompanying drawings show by way of illustration, and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense.

The embodiments disclosed herein reduce or substantially eliminate the need for site visits by pipeline/facility personnel to gather polarized pipe to soil readings (DC volts) and or AC voltage readings at individual test site locations. In particular, a system for testing cathodic protection levels on a metallic structure that is connected at a plurality of locations to one or more DC power sources is disclosed where each of the locations has one or more galvanic or impressed current anodes connected directly or indirectly to the metallic structure. The system includes one or more DC power supplies associated with each location, supplied either by galvanic anodes or impressed current anodes. An interrupter is operable to switch power on and off at each DC power supply. At each location a testing module measures a voltage differential between the metallic and an associated reference electrode at a plurality of points in time that span multiple cycles of power being synchronously switched on and off at each DC power supply. The testing module includes a memory for storing digital values indicative of the voltage differentials measured by the testing module. Each testing module includes data transfer capability and responds to a data request, by providing the stored digital values to a data collection module, which may be within an overhead aircraft or land based vehicle or carried by an individual.

Such a system permits owner operators of cathodically protected buried metallic structures such as pipelines to gather polarized potentials and/or AC voltage readings without having to synchronize test point recording modules with the interruption of power to the cathodic protection sources. The system operates to record a number of voltages per second for a set period of time. This set period of time exceeds the total cycle time of the cathodic protection interruption so that a number of interruption cycles are recorded. Included in these waveforms are the polarized potential readings that are required by regulation. The readings at each location may be conducted independent of any other location, thereby avoiding the need for synchronization between different locations. Such synchronization, which is commonly performed via GPS systems can be quite expensive.

For those structures where the current sources cannot be interrupted, an electronic switch permits readings to be taken on coupon test stations. This switch is activated prior to the waveform being collected allowing the recording of the polarization decay over the preset period of time.

As noted above, the systems and methods disclosed herein provide increased automation requiring less manpower for testing of cathodically protected structures. Moreover, the disclosed systems and methods reduce dependence of cathodically protected systems on interruption equipment from any given manufacturer/supplier of interruption equipment.

In one aspect, a method is disclosed for testing a cathodic protection system for a metallic structure which has associated therewith at each of a first set of locations, a testing module electrically connected to the metallic structure and an associated reference electrode. The method includes periodically, at a first frequency, interrupting power provided at each of the first set of locations to cause power provided to the metallic structure to switch on and off a plurality of times over a testing time period. Each testing module measures, a plurality of times during a plurality of interruption cycles, voltage differentials between the metallic structure and its associated reference electrode when the power provided to the metallic structure is on and when the power provided to the metallic structure is off. Initiation of each of the interruption cycles is independent of interrupting power provided at each of the first set of locations. Digital values associated with the measured voltage differentials during the interruption cycles are stored to a digital storage medium located at each testing module. The testing modules provide at least selected digital values to a remotely located device upon request by the remotely located device. The method may further include measuring, by each testing module, voltage differentials between the metallic structure and its associated reference electrode when the power provided to the metallic structure is on and when the power provided to the metallic structure is off is initiated after initiation of the testing time period. Further, the measuring, by each testing module of a voltage differential between the metallic structure and its associated reference electrode a plurality of times during a plurality of interruption cycles may be performed periodically at a frequency greater than the first frequency. The digital values provided to the remotely located device upon request may be digital values generated from the most recent interruption cycle. Any one of the locations may include a coupon, in which case measurements will be taken between the coupon and its associated reference electrode.

Also disclosed is a cathodic protection waveform monitoring unit comprising a first input adapted for electrical connection to a reference electrode associated with a location on a first metallic structure protected by a cathodic protection system. A second input is adapted for electrical connection to the first metallic structure. An A/D converter converts time varying analog voltage levels provided by the first and second inputs to digitally encoded values indicative of voltage levels between the first metallic structure and the reference electrode. The module includes data storage and a processor that is operatively coupled to the data storage. The processor is configured to execute instructions that when executed cause the processor to generate a first start test signal to store first digitally encoded values indicative of voltage levels during a period of time when a DC voltage applied to the first metallic structure is cycled on and off. The start test signal is generated independently of initiation of a period of time when a DC voltage applied to the first metallic structure is cycled on and off. The processor also generates a first stop test signal to stop storing the first digitally encoded values, and generates a response to an upload signal to cause transmission of at least a subset of the first digitally encoded values to a requesting device. The unit may include multiple channels to support readings from multiple metallic structures. Further, power scavenging may be employed to enhance battery life by generating power from ambient sources.

Additional aspects related to the invention will be set forth in part in the description which follows, and in part will be apparent to those skilled in the art from the description, or may be learned by practice of the invention. Aspects of the invention may be realized and attained by means of the elements and combinations of various elements and aspects particularly pointed out in the following detailed description and the appended claims.

FIG. 1 illustrates two underground pipelines 102 and 103 with cathodic protection and monitoring at a plurality of locations. In FIG. 1, underground pipelines 102 and 103 are associated with a plurality of test locations 104, 106 and 108. The pipelines 102 and 103 are disposed substantially parallel to each other in the portion shown in FIG. 1 and are shown for purposes of illustrating the capabilities and functions of the embodiments disclosed herein, which may operate in environments where there is only a single pipeline or more than two pipelines. The pipelines 102 and 103 are shown as examples of cathodically protected metallic structures. The embodiments disclosed herein may also operate in conjunction with other types of cathodically protected structures, such as for example, bridges. Three portions of the pipelines 102 and 103 are shown and such portions may be situated in proximity to one another or may be situated far apart from each other such as by tens or hundreds or more miles. For simplicity of illustration, the test locations 104, 106, 108 are shown generally in FIG. 1, with details of various embodiments shown in FIGS. 2A, 2B, 2C. Each test location may have associated therewith a terminal pair 112.1, 112.2 or 112.3 to which an external source of power may be connected. In the following description, elements designated with reference numbers ending in a suffix such as 0.1, 0.2, 0.3 may be referred to collectively by employing the main reference number without the suffix. For example, 112 refers to terminal pairs 112.1, 112.2 and 112.3 collectively. In an impressed current system a terminal pair 112 will be connected to an external source of power (not shown). In an impressed current system, a wire test lead 113.1, 113.2, 113.3 of the corresponding terminals 112.1, 112.2, 112.3 is connected to pipeline 102. A second wire test lead 123.1, 123.2, 123.3 of the corresponding terminals 112.1, 112.2, 112.3 is connected to pipeline 103. A third wire test lead 115.1, 115.2, 115.3 of the corresponding terminals 112.1, 112.2, 112.3 is connected to an associated permanent reference electrode 118.1, 118.2, 118.3 that is positioned underground. A fourth wire test lead 121.1, 121.2, 121.3 of the corresponding terminals 112.1, 112.2, 112.3 is connected to an associated permanent reference electrode 119.1, 119.2, 119.3 that is positioned underground. For an impressed current system, the source of power will often be an Alternating Current (AC) source, and in that event the test location (104, 106, 108) will have associated therewith a rectifier (not shown) to convert the AC power to Direct Current (DC). Each test location 104, 106, 108 also has associated therewith an interrupter (114.1, 114.2, 114.3) that operates to disconnect power from the test location to permit testing of the cathodic protection system. For an impressed current system, the interrupter operates to disconnect the external power source. For a galvanic system, the interrupter operates to disconnect the pipeline from an associated galvanic anode. The interrupters 114.1, 114.2, 114.3 may be one of a variety of conventional types which may operate independently of one another or may be synchronized across a protected structure (or portions thereof).

Also installed at each test location 104, 106, 108 is a CPWMU (120.1, 120.2, 120.3, generally 120) which operates in accordance with the principles described herein to provide pipe-to-soil (p/s) potential measurements of pipelines 102 and 103. Each CPWM 120 stores digital values indicative of the monitored waveforms as obtained via test lead pairs (such as 113, 115 or 123, 121 for CPWMU 120.1) and provides the same upon request from a Cathodic Protection Waveform Receiver (CPWR) 124 (seen specifically as 124.1, 124.2, 124.3). The CPWR 124 may be associated with an aircraft 126 which carries CPWR 124.1 or a vehicle 128 which carries CPWR 124.2 or a person carrying CPWR 124.3. The range over which communications between given CPWMU and a CPWR can vary and can be many miles, allowing data from a large number of CPWMU's to be retrieved by a single CPWR. For example, aircraft 126 may collect data from CPWRs spread over long distances, such as often occurs in rural areas, by flying in a generally parallel path to pipelines 102, 103. A vehicle 128 can collect data from CPWRs using access roads in remote areas and regular roadways in more populated areas without stopping to collect the data. An individual can carry a CPWR and collect data in urban areas and also in locations such as where many CPWMU's may be within communication capability such as from a hilltop.

Figure 2A:
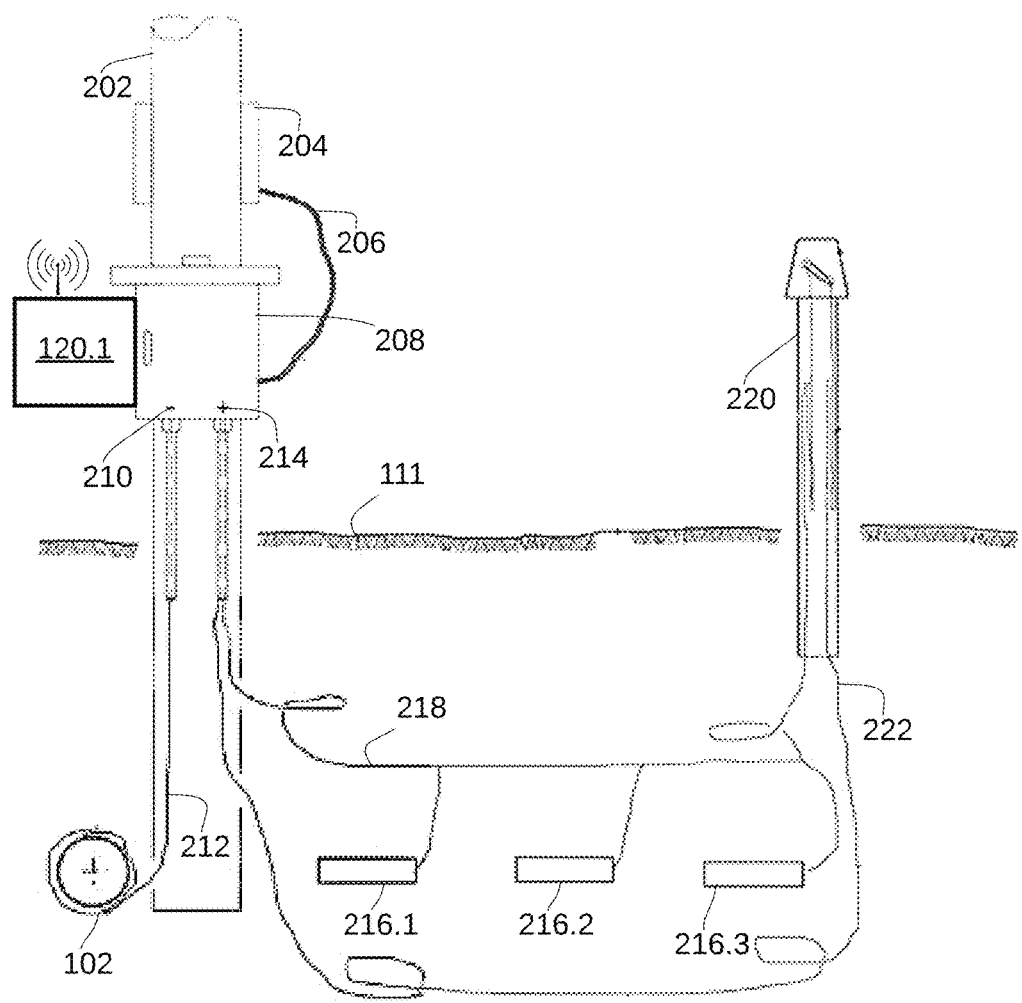
FIGS. 2A, 2B and 2C illustrate various embodiments of test locations for an underground pipeline with cathodic protection.
Figure 2B:
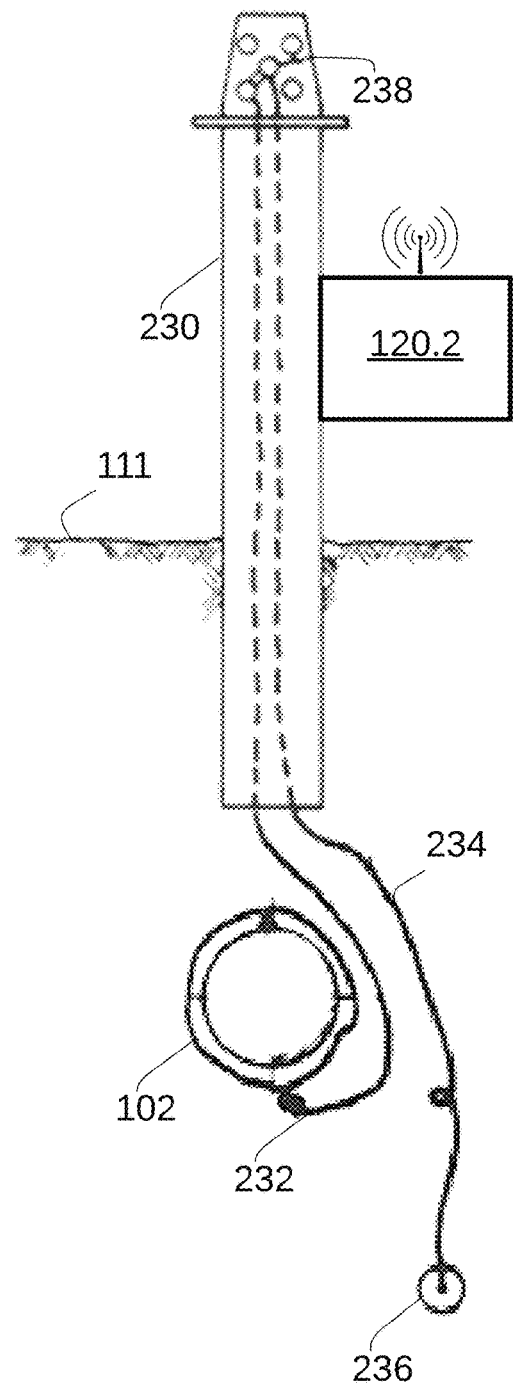
Figure 2C:
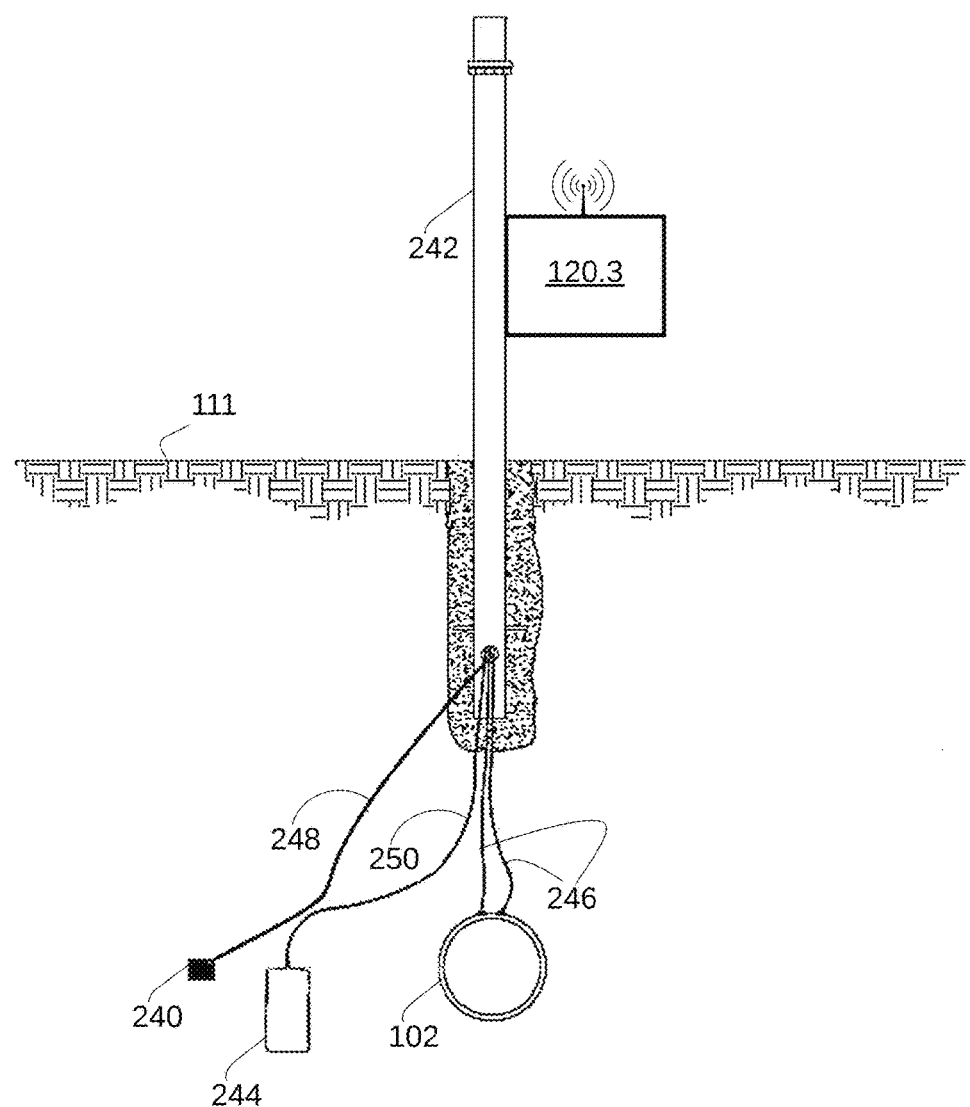

FIGS. 2A, 2B and 2C illustrate various embodiments of a test location such as 104, 106, 108 for an underground pipeline with cathodic protection. FIG. 2A illustrates an embodiment of an impressed current cathodic protection system in which a power pole 202 is connected to a source of electrical energy provided via service panel 204 which supplies AC power via electrical connection 206 to a rectifier 208, positioned within the power pole 202, which converts the AC power to DC. The power pole 202 extends beneath the ground surface 111. Pipeline 102 is shown in cross-section and is electrically connected to negative terminal 210 of rectifier 208 via wire 212. The positive terminal 214 of the rectifier 208 is electrically connected to several anodes 216.1, 216.2, 216.3 via wire 218. The anodes 216 are metallic elements positioned underground, i.e. below ground surface 111. Three anodes 216 are shown but more or less can be used depending on the amount of current required to provide cathodic protection to pipeline 102. Also, shown in FIG. 2A is test station 220 which operates to permit testing of the integrity of underground wire 218. As seen, the test station 220 contains wiring 222 that is connected to the anodes 216 and to the cathode 214 of rectifier 208. As seen by way of example, CPWMU 120.1 is associated with the embodiment of FIG. 2A.

FIG. 2B illustrates an embodiment of a galvanic cathodic protection system in which a test station 230 is positioned to extend beneath ground surface 111 to provide cathodic protection to buried pipeline 102 (shown in cross-section). Pipeline 102 is electrically connected via wires 232, 234 to a galvanic anode 232 (shown in cross-section) that is positioned below ground surface 111. The wires 232, 234 are electrically connected within test station 230 via shorting strap 238. The galvanic anode 232 is formed of a material the provides a lower (that is, more negative) electrode potential than that of the pipeline 102. This causes the potential of the steel surface of pipeline 102 to be polarized (pushed) more negative until the surface has a uniform potential which removes the driving force for corrosion reaction on the surface of pipeline 102. As seen by way of example, CPWMU 120.2 is associated with the embodiment of FIG. 2A.

FIG. 2C illustrates an embodiment of a cathodic protection system similar to the embodiment of FIG. 2B but employing a coupon 240. Test station 242 is positioned to extend beneath ground surface 111 to provide cathodic protection to buried pipeline 102 (shown in cross-section). Pipeline 102 is electrically connected via wires 246, 250 to a galvanic anode such as 244 (shown in cross-section) that is positioned below ground surface 111, and to a coupon 240 via wire 248. The wires 246, 248, 250 are electrically connected within test station 242 via a shorting strap (not shown). Wires 246 are duplicated for reliability and ease of maintenance should one wire fail. The galvanic anode 244 is formed of a material the provides a lower (that is, more negative) electrode potential than that of the pipeline 102. This causes the potential of the steel surface of pipeline 102 to be polarized (pushed) more negative until the surface has a uniform potential which removes the driving force for corrosion reaction on the surface of pipeline 102.

Coupon 240 operates to simulate an uncoated part of pipeline 102 and thereby provides an alternative measurement for evaluating the effectiveness of a cathodic protection system. Coupon 240 takes the form of a piece of metal that is electrically connected to pipeline 102. The electrical potential at coupon 240 closely approximates the potential of any exposed portion of the pipeline 102 located in the vicinity of coupon 240. The permanent reference electrode 244 standardizes the potential measurements at all test locations. There is a voltage (IR) drop that exists in the soil or across the coating that produces an error in the pipe-to-soil (p/s) potential measurement. This error varies from pipeline to pipeline and even along the length of a given pipe. This IR-drop is affected by soil resistivity, depth of burial, coating condition, and amount of (Cathodic Protection) CP current. Generally, this IR-drop may be corrected by interrupting the CP current and measuring an off-potential immediately following interruption. The off-potential measured by interruption is an estimate of the polarized potential of the pipe. The question with any measurement is how accurately does it estimate the desired parameter. There are a number of problems with the off-potential method, although it continues to be the best method available and has proven to be a very useful measurement when all current is interrupted. The problems include: (a) current from multiple rectifiers must be interrupted simultaneously (or a non-synchronous interruption method such as with a coupon as shown in FIG. 2(C), (b) often, second party CP systems are present in the area that are either unknown or cannot be interrupted and these systems can introduce IR-drop errors in the off-potential measurement, (c) fixed sacrificial anodes are often included as hot spot protection for a variety of reasons that can produce errors in the off-potential measurement, (d) long-line currents have been shown to produce errors that interruption cannot eliminate, (e) stray current situations can cause significant errors in the off-potential measurement, (f) rapid IR transients (spikes), immediately following interruption, can cause errors in the off-potential measurement, (g) simple averaging over some area of pipe, due to pipe to soil potential measurements made at grade, can cause local potential fluctuations to be under estimated, and (h) multiple pipelines in the same right-of-way can produce averaging of the multiple lines preventing an accurate measure of any given line.

Figure 3A:
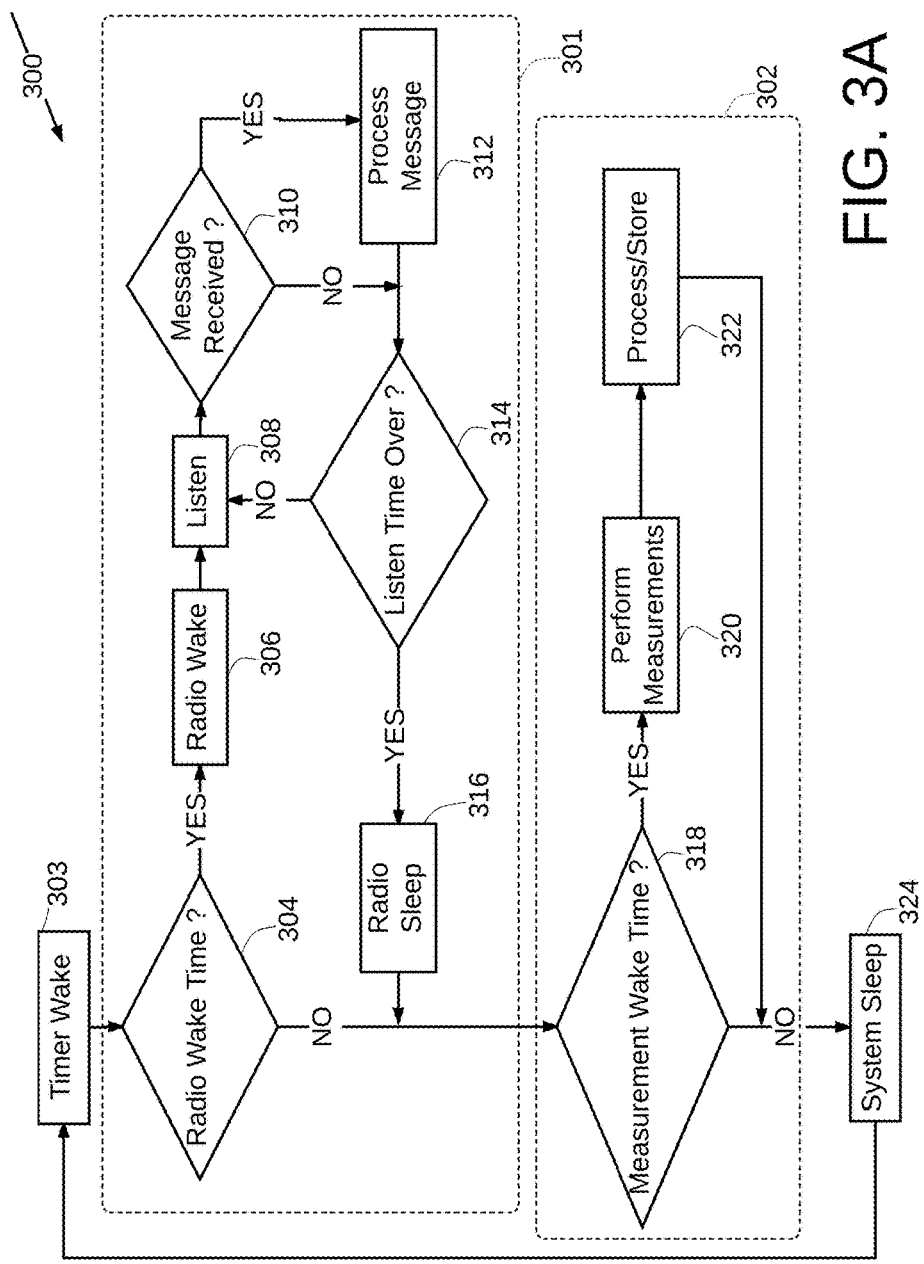
FIG. 3A is a flowchart illustrating operation of an embodiment of a Cathodic Protection Waveform Monitoring Unit (CPWMU).

FIG. 3A is a flowchart illustrating operation of an embodiment of a Cathodic Protection Waveform Monitoring Unit (CPWMU) 120. The CPWMU 120 performs the steps shown in routines 301 and 302 periodically as a function of a programmable timer shown at 303, that may be programmed to cause the CPWMU 120 to awaken and cause appropriate checks at steps 304 and 318 to determine if routines 301 and/or 302 require execution. The programmable timer may be set via digital values entered into the CPWMU 120 to wake approximately for example, every 15 seconds. Longer or shorter intervals may also be selected. Routine 301 operates to transmit stored data that is indicative of potential measurements from the structures 102, 103 to the associated reference electrodes 118, 119. Routine 302 operates to collect the stored data indicative of potential measurements from the structure being measured.

In data transmit routine 301, a radio wake time is tested at step 304 to determine if communication with a CPWR 124 is required. At step 306, a radio in the CPWMU is awakened (activated) and a listening/transmission loop comprising steps 308, 310, 312 and 314 is executed. At step 308, the CPWMU 120 listens over its radio to determine, step 310, if a message from a CPWR to transmit data has been received. The listen time is programmable. If a message has been received then the message is processed at step 312 and data that has been requested by the requesting CPWR is transmitted by the CPWMU 120 to the requesting CPWR 124. If a message has not been received at step 310 then a test is performed at step 314 to determine if the programmed listen time has expired. If not, then the listening/transmission loop continues to execute. If the listen time has expired then at step 316 the radio is turned off (put into sleep mode) to conserve power, and the CPWMU continues to the measurement routine 302.

In measurement routine 302, at step 318, a test is performed to determine if a measurement interval is to commence. The measurement intervals are executed at programmable time intervals depending on how frequently measurements of the system 100 are desired. The frequency with which measurements are performed will be a function of a variety of factors including regulatory requirements, perhaps environmental factors, pipeline history and also battery life of the CPWMU. For example, some CPWMU's may be programmed for the measurement routine 302 to be executed once a month. If the measurement interval is determined to be started at 318 then at 320 the required measurements are performed by converting the sensed voltages into digital values. In certain embodiments, other measurements such as temperature may also be sensed, converted to digital values and stored. At step 322, the digital values are optionally further processed by for example, mathematical scaling and digital filtering for DC/low frequency measurements, and also including calculations such as peak to peak represented voltage and RMS represented voltage for AC measurements. In certain embodiments, estimation of AC frequency is another process step which may be added for AC measurements. The processed digital values are then stored at 322 to digital storage. At 324 the CPWMU 120 goes to sleep until a wake time is indicated at 303 by the timer. Software code to perform the steps shown in FIG. 3A is stored in firmware in a first embodiment.

Figure 5:
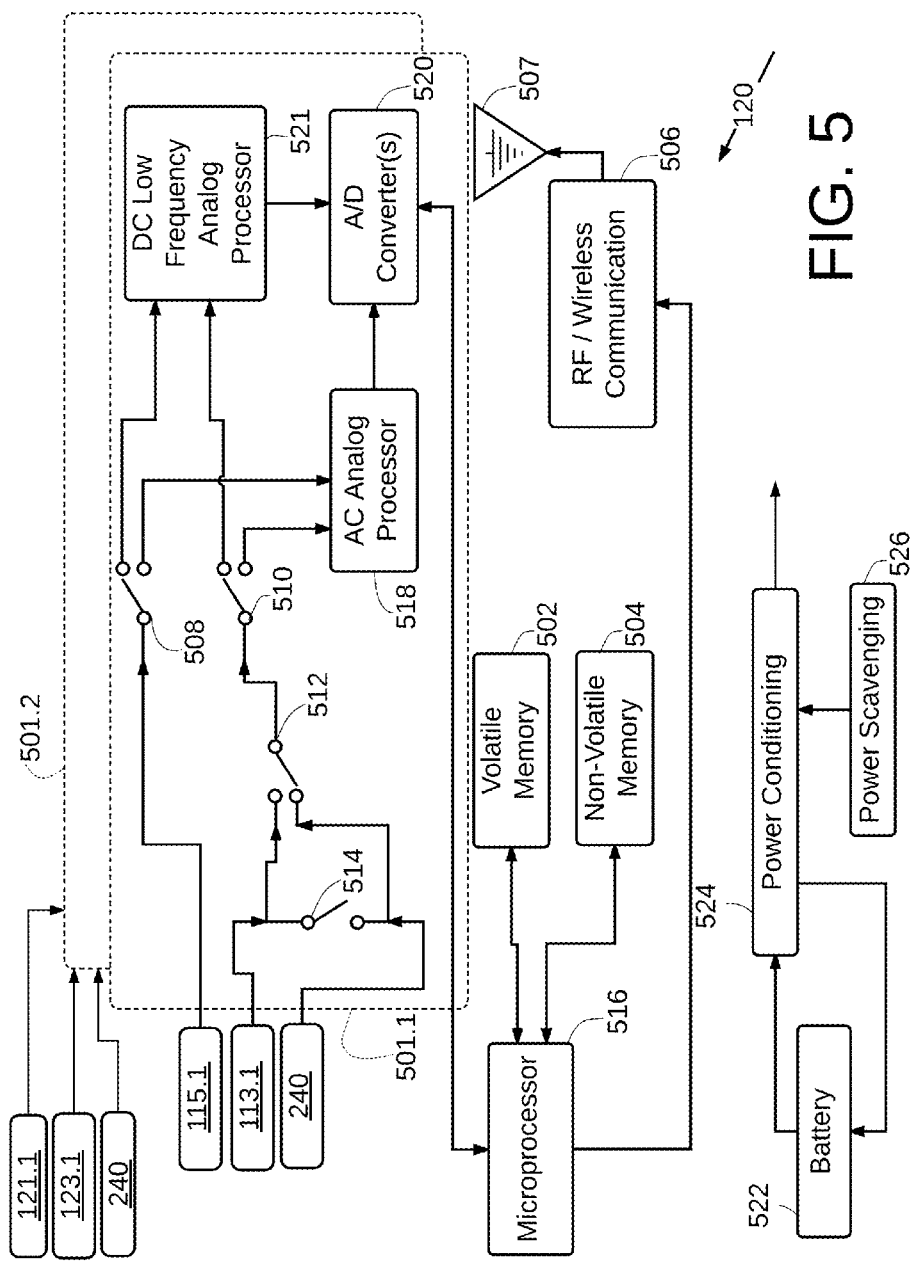
FIG. 5 is a block diagram of hardware elements of an embodiment of a CPWMU.

In a multichannel system such as shown in FIG. 5 with channels 501.1 and 501.2, the measurement routine 302 can be performed concurrently for both channels or alternatively may be performed independently for each channel. If the measurement routine 302 is performed independently then the measurement wake time 318 may be different for each channel.

Figure 3B:
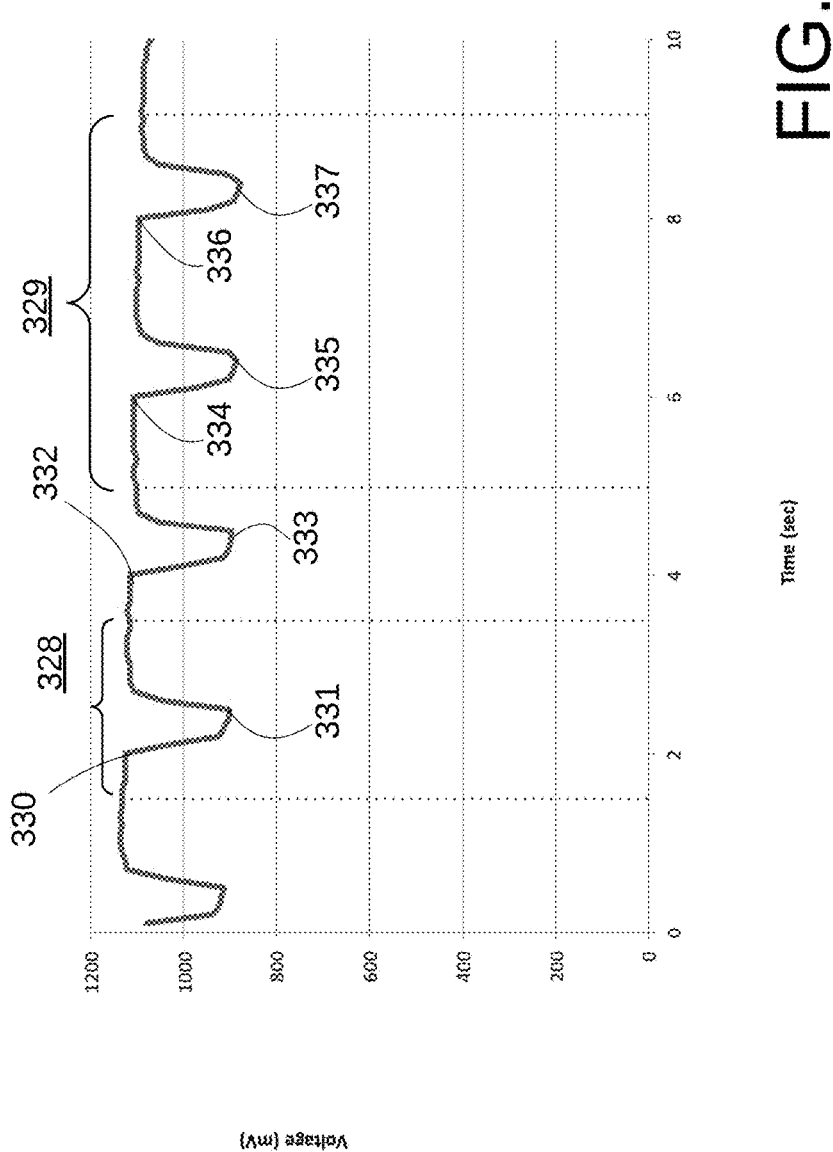
FIG. 3B is a graph illustrating a waveform measured by a CPWMU.

Operation of the measurement routine 302 may be better understood by referring to FIG. 3B which shows a graph of potential measurements, such as from pipeline 102 to an associated reference electrode such as for example, pipeline 102 to reference electrode 118.1. FIG. 3B shows voltages (in millivolts (mV)) from potential differentials from, for example, pipeline 102 to electrode 118.1, along the vertical axis varying over time, (in seconds (sec)) shown on the horizontal axis. The voltage variations shown in FIG. 3B are the result of power interruptions by an interrupter, such as 114.1, to permit testing by a CPWMU, such as 120.1, of cathodic protection to the protected structure, such as pipeline 102. As seen in FIG. 3B at 330, when interrupter, such as 114.1, operates to interrupt power between reference electrode 118.1 and test lead 113.1 the potential between 118.1 and 113.1 drops from approximately 1100 mV to approximately 900 mV until the interrupter 114.1 causes 118.1 and 113.1 to be electrically connected. Additional interrupter-on, interrupter-off pairs, are shown at (332, 333), (334, 335) and (336, 337). The time from one interruption to the next, such as from 330 to 332 is the total cycle time of the cathodic protection interruption.

A CPWMU as disclosed herein, operates to sample the potential difference on a protected structure (such as potential difference between 118.1 and 113.1 on structure 102) by sampling the potential difference multiple times over an interruption cycle, such as shown at 328 and 329. Interruption cycle 328 spans approximately two seconds and interruption cycle 329 spans approximately four seconds. These periods of time are purely for purposes of illustration and a CPWMU 120 as disclosed herein may be programmed with other periods of time for an interruption cycle. The CPWMU 120 takes and stores multiple samples, such as 10 samples per second, over an interruption cycle, so twenty samples will be taken for interruption cycle 328. As seen the interruption cycles are independent of the total cycle time of the cathodic protection interruption, both in the initiation of the interruption cycle and in the length of the interruption cycle. The sampling frequency may be higher or lower for interruption cycle 329. In certain embodiments, the CPWMU 120 may be programmed to identify interruption cycles in which at least one interrupter-on, interrupter-off pair occurs and to store only samples spanning such pairs to avoid storage of unnecessary data and thereby permit a CPWMU 120 to require less data storage capacity.

An advantage of the CPWMUs disclosed herein is that an interruption cycle need not be synchronized with operation of an associated interrupter. The CPWMU 120 may therefore operate independently of the interrupter. For example, a CPWMU 120 may be programmed to execute routine 302 every twenty-four hours for two minutes. The measurement wake time at step 318 would cause the routine 302 to be executed at a predetermined time every twenty-four hours for a predetermined period of time. If a cathodic protection system for a protected structure is designed to test the system say once per month, for example, by causing interrupters 114 to interrupt power on the first day of the month for four hours, the CPWMUs will collect multiple samples of data over multiple interruption cycles without being synchronized to the power interruptions. Interruption of power need not be synchronized across multiple test locations (such as 104, 106, 108) on a protected structure, thereby avoiding the need for expensive upgrades to existing cathodic protection systems. A further advantage is that installation of the CPWMU 120 onto existing cathodic protection systems is simplified by eliminating the need to modify or update existing cathodic protection systems. The cost and time savings can be significant over a protected structure such as a pipeline which may span hundreds or thousands of miles. The frequency with which measurement routine 302 is executed, and the time span over which it is executed, is a matter of design choice and may be a function of (i) the specifics of the cathodic protection system on which the CPWMU 120 in question is installed, such as frequency of the cathodic protection system test, and (ii) the specifics of the CPWMU 120 such as power availability (if battery powered) and data storage capability.

FIG. 4 is a flowchart illustrating operation of an embodiment of CPWR 124 to execute a data collection routine 400. The CPWR 124 preferably operates in accordance with a variety of settings established by an external computing device (shown in FIG. 6), as seen at 402. Such settings may include measurement interval, duration, sample rate, voltage type, high or low range DC. At 404, the CPWR 124 transmits a unique reading run key to CPWMU 120 to cause initiation by the CPWMU 120 of the transmit routine 301. This unique reading run key in certain embodiments is based in part by the external computing device's internal date and time. At 406, a receiver at the CPWR 124 is activated and at step 408 a query based on the unique run key is performed to determine if data from a CPWMU 120 is to be received. At 410, a data transmission protocol is employed to request, accept and acknowledge data between the CPWMU 120 and the CPWR 124. The data included may also include date, time, software updates and CPWMU 120 settings such as the radio wake time 304 and the measurement wake time 318. At 412, the received data is stored, and provided to an external computing device for storage in a database.

A reading run key transmitted by a CPWR 124 may be received by more than one CPWMU 120, which will cause transmission by more than one CPWMU 120, via routine 301, of data requested by the CPWR 124. In such an event, the CPWR 124 will accept data in the order received. Each CPWMU 120 has associated therewith a unique ID to enable the CPWR 124 to identify data as received from the appropriate CPWMU 120. A conventional contention mechanism may be employed to handle collisions in transmission by multiple CPWMUs. In certain embodiments, the CPWMU 120 will retain data collected from interruption cycles until the non-volatile memory 504 reaches capacity and will then overwrite the oldest data. When interrogated by the CPWR 124, the CPWMU 120 will provide data from the most recent interruption cycle reading, or in other embodiments, several recent interruption cycle readings. The data collection routine 400 will typically be initiated manually by an operator of the CPWR 124 to cause collection of data from one or more CPWMUs.

FIG. 5 is a block diagram of hardware elements of an embodiment of a CPWMU 120. The CPWMU 120 records voltage waveforms at user programmed intervals and duration, which are then recorded in the CPWMU's memory. The waveforms are saved in memory 502, 504 until the CPWMU 120 is polled by the CPWR 124. Once polled the CPWMU 120 transmits the stored information via any one of several communication systems (seen generally at 506 and 507) to CPWR 124. The information may be retrieved via aircraft, helicopter, UAV or land based methods of transportation depending on the location of the CPWR 124 and the communication capabilities (eg. range) of the CPWM 120 and CPWR 124 in question.

The CPWMU 120 as shown in FIG. 5 has three inputs per channel (and two channels 501.1 and 501.2) adapted to be connectable to a reference cell 118, such as copper-copper sulfate, via leads 115.1 or 121.1, a pipeline or object, such as pipeline 102 via leads 113.1 or 123.1 and an optional coupon, such as coupon 240. The type (AC or DC) and termination points of voltage reading are programmable and are controlled by electronic switches 508, 510, 512, 514 in conjunction with the microprocessor 516, AC analog processor 518, DC low frequency analog processor 520, and analog to digital converter 520. The exact components used are determined by the user's preferences. For example, if AC voltage is selected then the AC analog processor 518 and the analog to digital converter 520 are used, if DC voltage is selected then the DC low frequency analog processor 521 and analog to digital converter 520 are used. The multiple channels 501.1 and 501.2 permit a single CPWMU 120 to monitor multiple protected structures such as seen in FIG. 1 where a single CPWMU (120.1, 120.2, 120.3) monitors cathodic protection on the two pipelines 102 and 103. The embodiment shown in FIG. 5 has two channels, 501.1 and 501.2. Other embodiments may have only a single channel, or three or more channels. Channel 501.2 replicates the hardware components shown for channel 501.1.

DC low frequency analog processor 521 operates to filter out higher frequency AC components, for example 50-60 Hz from nearby powerlines and in certain embodiments to adjust, such as by amplifying or reducing, voltage levels. AC analog processor 518 operates as a band pass filter to remove low frequency signals such as from nearby motors. In certain embodiments, processor 518 can also add DC offset levels and thereby reduce the need for additional voltage conversion that would consume more power. The processor 518 may also operate to amplify or attenuate the signal. The A/D converter 520 operates to convert incoming analog signals to digital values for processing as necessary by microprocessor 516 and storage in memory 502 and/or 504. The hardware components in FIG. 5 are shown separately for purposes of explanation of the functions performed but may be integrated depending on the needs of a particular design. For example, the functions performed by A/D converter 520 may be integrated into microprocessor 516 as may the functions performed by one or more of the other hardware elements shown in FIG. 5.

The RF/wireless communication 506 and the antenna 507 are controlled by the microprocessor 516 to intermittently monitor the radio environment around the CPWMU 120 to determine if it is being polled by the CPWR 124. Once contact is confirmed the microprocessor 516 through the RF/wireless communication 506 and antenna 507 transmits the stored information to the requesting CPWR 124. The design of the communication circuitry 506 and antenna 507 will vary depending on communication range required and power consumption. The CPWMU 120 preferably combines the option of a number of communication technologies including analog or digitally modulated radio and extremely low power usage use components in a multichannel data logger system which automatically captures the polarized potentials (on and off) and AC voltage readings of synchronized interrupted cathodically protected facilities. The microprocessor 516 operates via programmed instructions to control the operation of the various components of the CPWMU 120. The connections among the components in FIG. 5 are shown in simplified form for purposes of explanation.

As shown in FIG. 5, switch 512 selects between lead 113.1 from pipeline 102, and a coupon 240 (if present). Switch 514 operates to switch off the CPWMU lead for a coupon if no coupon is present. The selected input (pipeline lead 113.1 or coupon 240) is provided by selector 510 to either AC analog processor 518 or to DC low frequency analog processor 521 depending on the nature of the signal being recorded. Reference electrode input 115.1 is similarly provided via selector 508 to AC analog processor 518 or DC low frequency analog processor, the outputs of which are converted by A/D converter(s) 520 to digital values for storage in memory 502 and/or 504.

The CPWMU 120 will typically be powered by a battery 522 which provides power via power conditioning circuitry 524. An external power source (not shown) may also be employed as a primary or secondary source of power. Battery life for a CPWMU 120 is typically an important consideration to operators of protected structures such as pipelines so the CPWMU 120 may be programmed to reduce the frequency with which measurement routine 302 is executed. Additionally, the CPWMU 120 may employ one or more sources of supplemental power by various types of power scavengers 526. Power scavenging, also referred to as power or energy harvesting operates to derive energy from external ambient sources such as solar, thermal, wind, and temperature. For example, power scavenger 526 may take the form of solar panels to provide solar generated energy. Power generated from vibration, such as from a motor (if present), or if the protected structure is a bridge, then from traffic may also be employed. Power scavenging may also be obtained from temperature differentials (such as between pipeline 102/103 and ground or air temperature. Low voltage AC currents that may be present may also be scavenged for power.

Figure 6:
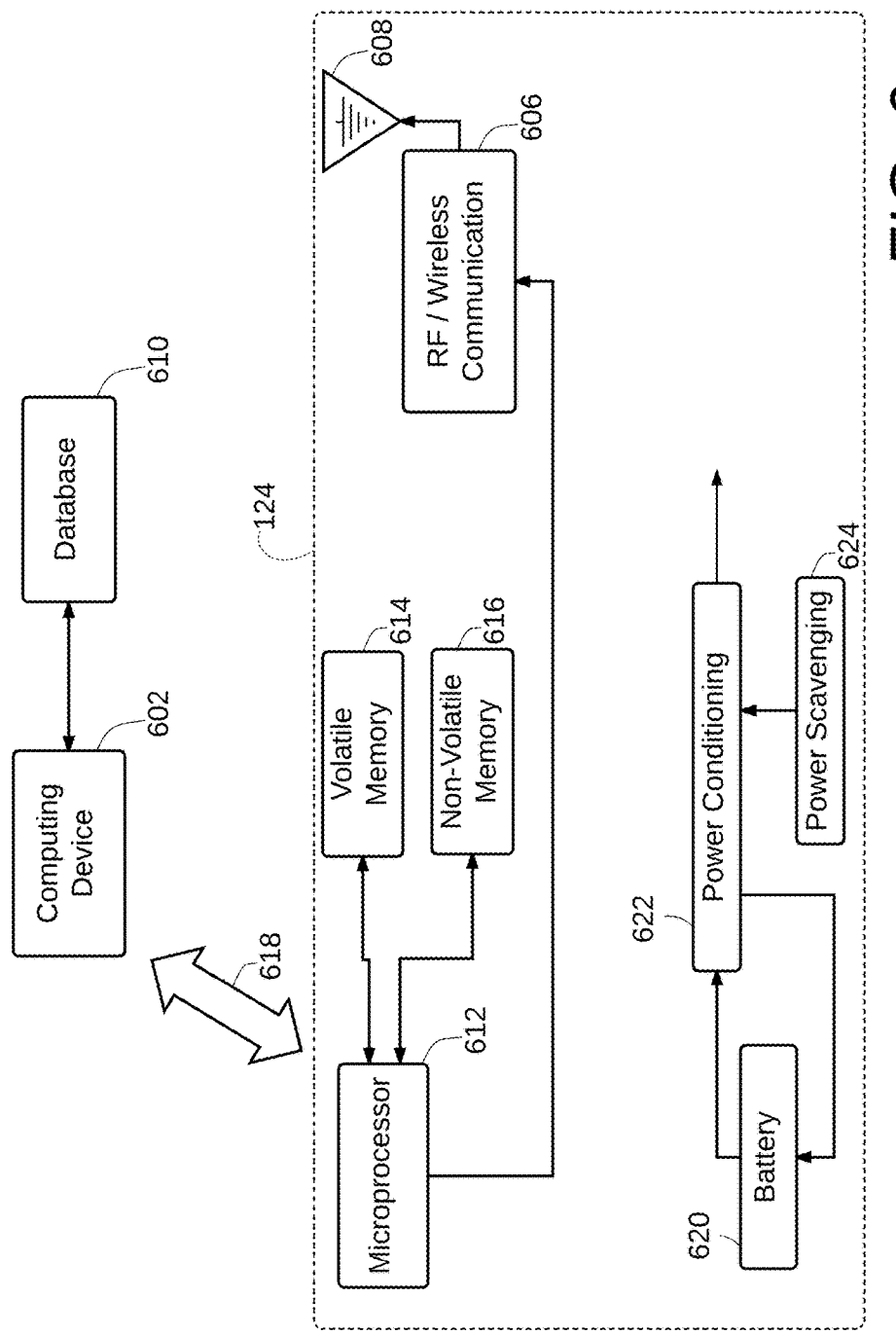
FIG. 6 is a block diagram of hardware elements of an embodiment of a CPWR.

FIG. 6 is a block diagram of hardware elements of an embodiment of a CPWR 124. The CPWR 124 communicates with an external computing device 602 to transfer stored data to a database 610. When used in the CPWR 124, the microprocessor 612 in the CPWR 124 is programmed such that when connected to the external computing device 602 it will ignore all of the components with the exception of the memory 614, 616, the RF/wireless communication 606 and the antenna 608. These components are required to receive the information from the CPWMU(s) 120 in the field. The CPWR 124 may be powered as seen in FIG. 6 in the same manner as described in connection with FIG. 5 or be powered by the external computing device or other vehicular power source. Computing device 602 may be a conventional computing device such as a laptop computer or other portable device such as a tablet or mobile phone and may connect to CPWR 124 via connection 618 which may take the form of a wired connection such as USB or a conventional wireless connection.

Microprocessors 516 and 612 execute computer-executable instructions and can be a general-purpose central processing unit (CPU), processor in an application-specific integrated circuit (ASIC) or any other type of processor. The volatile memory 502, 614 may take a variety of forms including registers, cache or RAM. The non-volatile memory 504, 616 may take a variety of forms including ROM, EEPROM, flash memory or some combination accessible by the microprocessors 516 and 612. The hardware components in FIGS. 5 and 6 may be standard hardware components, or alternatively, some embodiments may employ specialized hardware components to further increase the operating efficiency and speed with which the system 100 operates.

The CPWMU 120 and CPWR 124 may have additional features such as, for example, additional input devices and output devices (not shown). The interconnections between the various components shown in FIGS. 5 and, 6 are shown for the purpose of explanation and may take various forms including various direct connections or shared communication mechanism such as a bus, controller, or network that interconnects the components shown. Typically, operating system software (not shown) provides an operating system for other software executing in the CPWMU 120 and CPWR 124, and coordinates activities of the various components in the system. The non-volatile memory 504, 616 stores the operating system and instructions for the software implementing one or more innovations described herein.

The communication connection(s) 506/507 and 606/608 enable communication over a communication medium to another computing entity and convey information such as computer-executable instructions, or other data in a modulated data signal. A modulated data signal is a signal that has one or more of its characteristics set or changed in such a manner as to encode information in the signal. By way of example, and not limitation, communication media can use an electrical, optical, RF, or another carrier.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

What is claimed is:

1. A method for testing a cathodic protection system for a metallic structure that has associated therewith a first set of locations, each location of the first set of locations including a testing module, electrically connected to the metallic structure, and an associated reference electrode, the method comprising, for each location of the first set of locations:
   periodically, at a first frequency, interrupting power provided at each location of the first set of locations to cause power provided to the metallic structure to switch on and off a plurality of times over a testing time period;
   measuring, by each testing module, DC voltage differentials between the metallic structure and its associated reference electrode when the power provided to the metallic structure is on and when the power provided to the metallic structure is off, at a plurality of times during a plurality of interruption cycles, wherein measuring DC voltage differentials between the metallic structure and its associated reference electrode when the power provided to the metallic structure is off is asynchronous to interrupting power to the metallic structure, and wherein initiation of each of the interruption cycles is independent of interrupting power provided at each location of the first set of locations;
   storing in a digital storage medium at each testing module, digital values associated with the measured DC voltage differentials during the interruption cycles; and
   providing at least selected digital values to a remotely located device upon request by the remotely located device.

2. The method set forth in claim 1 wherein measuring, by each testing module, DC voltage differentials between the metallic structure and its associated reference electrode when the power provided to the metallic structure is on and when the power provided to the metallic structure is off, at a plurality of times during a plurality of interruption cycles, is initiated after initiation of the testing time period.

3. The method set forth in claim 1 wherein measuring, by each testing module, DC voltage differentials between the metallic structure and its associated reference electrode when the power provided to the metallic structure is on and when the power provided to the metallic structure is off, at a plurality of times during a plurality of interruption cycles, is performed periodically at a frequency greater than the first frequency.

4. The method set forth in claim 1 wherein providing at least selected digital values to a remotely located device upon request by the remotely located device comprises providing digital values generated from the most recent interruption cycle.

5. The method set forth in claim 1 wherein the cathodic protection system further comprises a second set of locations that each include a testing module electrically connected to a coupon and an associated reference electrode, the method further comprising, for each location of the second set of locations:
- measuring, by each testing module at the second set of locations, a DC voltage differential between the coupon and its associated reference electrode, during at a plurality of times during a plurality of interruption cycles;
- storing in a digital storage at each testing module at the second set of locations, digital values associated with the measured DC voltage differentials during the measurement time period; and
- providing at least selected ones of the digital values to a remotely located device upon request by the remotely located device.

6. A system for testing cathodic protection potential on a metallic structure at a plurality of locations, wherein each of the locations has one or more galvanic or impressed current anodes connected to the metallic structure, the system comprising, at least at a subset of the locations:
- an interrupter at each location operable to periodically switch electrical energy applied to the metallic structure on and off;
- testing means for measuring a DC voltage differential between the metallic structure, or alternatively a metallic coupon if installed at a location with which the testing means is associated, and an associated reference electrode, at a plurality of points in time that span multiple cycles of power being switched on and off by the interrupter, wherein the testing means measures the DC voltage differential when the power is switched off by the interrupter at one or more points in time that are asynchronous with the power being switched off by the interrupter;
- data storage for storing digital values indicative of the DC voltage differentials measured by the testing means; and
- data transfer means, responsive to a data request, for providing a selected subset of the stored digital values to a remote device.

7. The system of claim 6 wherein the selected subset of the stored digital values comprises values corresponding to a timestamp indicative of most recently stored values.

8. The system of claim 6 wherein the data transfer means provides the selected subset of the stored digital values wirelessly to the remote device.

9. The system of claim 6 wherein the testing means for measuring a DC voltage differential between the metallic structure, or alternatively a metallic coupon if installed at a location with which the testing means is associated, and an associated reference electrode operates independently of the interrupter.

10. The system of claim 6 wherein the testing means operates at a frequency to measure the voltage differential multiple times during an interruption cycle.

11. The system of claim 6 wherein the testing means, data storage and data transfer means are powered independently of the electrical energy applied to the metallic structure.

12. The method of claim 1 wherein the providing at least selected digital values to a remotely located device upon request by the remotely located device is performed by wirelessly transmitting the selected digital values.

13. The method of claim 1 wherein interrupting power provided at each location of the first set of locations to cause power provided to the metallic structure to switch on and off a plurality of times over a testing time period is performed synchronously across the first set of locations.

14. The method of claim 1 wherein interrupting power provided at each location of the first set of locations to cause power provided to the metallic structure to switch on and off a plurality of times over a testing time period is performed asynchronously across the first set of locations.

15. A method for testing a cathodic protection system for a metallic structure, that has associated therewith at each of a first set of locations, a testing module electrically connected to the metallic structure and an associated reference electrode, the method comprising:
- periodically, at a first frequency, interrupting power provided at each of the first set of locations to cause power provided to the metallic structure to switch on and off a plurality of times over a testing time period;
- measuring at each location of the first set of locations, by an associated testing module, voltage differentials between the metallic structure and its associated reference electrode when the power provided to the metallic structure is on and when the power provided to the metallic structure is off, a plurality of times, wherein measuring of the voltage differentials at each location when power provided to the metallic structure is off is performed asynchronously to the interrupting of power at each location;
- storing in a digital storage medium at each testing module, digital values associated with the measured voltage differentials; and
- providing at least selected digital values to a remotely located device upon request by the remotely located device.

16. The method of claim 15 wherein measuring of the voltage differentials at each location is performed at a frequency that is different than the first frequency.

17. The system of claim 6 wherein the testing means comprises a processor operatively coupled to the data storage, the processor configured to execute instructions that when executed cause the processor to:
- generate a first start test signal to cause storage to the data storage, first digitally encoded values indicative of voltage levels during a period of time when electrical energy applied to the metallic structure is cycled on and off, wherein the start test signal is generated independently of cycles of power being switched on and off by the interrupter;
- generate a first stop test signal to stop storing the first digitally encoded values to the data storage; and generate a response to an upload signal to cause transmission by the data transfer means of at least a subset of the first digitally encoded values to a requesting device.

18. The system of claim 17 wherein the processor is further configured to execute instructions that when executed cause the processor to:
generate a command to overwrite the oldest first digitally encoded values when the data storage is at capacity.

19. The system of claim 17 wherein the metallic structure corresponds to a first metallic structure and wherein the system is configured to test cathodic protection potential on a second metallic structure at a plurality of locations, wherein each of the locations of the second metallic structure has one or more galvanic or impressed current anodes connected to the second metallic structure and wherein the processor is further configured to execute instructions that when executed cause the processor to:
generate a second start test signal to store to the data storage, second digitally encoded values indicative of voltage levels during a period of time when electrical energy applied to the second metallic structure is cycled on and off, wherein the second start test signal is generated independently of cycles of power being switched on an off by the interrupter;
generate a second stop test signal to stop storing the second digitally encoded values to the data storage; and
generate a response to an upload signal to cause transmission by the data transfer means of at least a subset of the second digitally encoded values to a requesting device.

* * * * *